United States Patent
Naitou et al.

(10) Patent No.: US 10,550,078 B2
(45) Date of Patent: Feb. 4, 2020

(54) METHOD FOR PRODUCING FLUOROPOLYOXYALKYLENE PEROXIDE COMPOUND

(71) Applicant: DAIKIN INDUSTRIES, LTD., Osaka-shi, Osaka (JP)

(72) Inventors: Masato Naitou, Osaka (JP); Takashi Nomura, Osaka (JP); Shinya Takano, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 16/314,955

(22) PCT Filed: Jul. 4, 2017

(86) PCT No.: PCT/JP2017/024535
§ 371 (c)(1),
(2) Date: Jan. 3, 2019

(87) PCT Pub. No.: WO2018/008648
PCT Pub. Date: Jan. 11, 2018

(65) Prior Publication Data
US 2019/0308936 A1    Oct. 10, 2019

(30) Foreign Application Priority Data
Jul. 5, 2016    (JP) ................. 2016-133208

(51) Int. Cl.
C07C 407/00    (2006.01)
C07C 409/20    (2006.01)
C08G 65/00    (2006.01)
C08G 65/324    (2006.01)

(52) U.S. Cl.
CPC .......... *C07C 407/00* (2013.01); *C07C 409/20* (2013.01); *C08G 65/324* (2013.01)

(58) Field of Classification Search
CPC .... C07C 407/00; C07C 409/20; C08G 65/324
See application file for complete search history.

(56) References Cited

U.S. PATENT DOCUMENTS

| | | | | |
|---|---|---|---|---|
| 5,149,842 A | * | 9/1992 | Sianesi | C08G 65/007 549/550 |
| 5,258,110 A | * | 11/1993 | Sianesi | C08G 65/007 204/157.92 |
| 5,354,922 A | * | 10/1994 | Marchionni | C08G 18/5015 204/157.92 |
| 5,783,789 A | | 7/1998 | Guarda et al. | |

FOREIGN PATENT DOCUMENTS

JP    9-227507 A    9/1997

OTHER PUBLICATIONS

International Preliminary Report on Patentability with translation of Written Opinion dated Jan. 17, 2019, issued by the International Searching Authority in application No. PCT/JP2017/024535.

* cited by examiner

*Primary Examiner* — Sikarl A Witherspoon
(74) *Attorney, Agent, or Firm* — Sughrue Mion, PLLC

(57) ABSTRACT

A method for producing a fluoropolyoxyalkylene peroxide compound containing one or more —$CF_2OOCF_2O$— units, which includes treating a fluoropolyoxyalkylene compound containing two or more —$CF_2O$— units in the presence of an oxygen source.

15 Claims, No Drawings

METHOD FOR PRODUCING FLUOROPOLYOXYALKYLENE PEROXIDE COMPOUND

This Application is a National Stage of International Application No. PCT/JP2017/024535 filed Jul. 4, 2017, claiming priority based on Japanese Patent Application No. 2016-133208 filed Jul. 5, 2016.

TECHNICAL FIELD

The present invention relates to a method for producing a fluoropolyoxyalkylene peroxide compound.

BACKGROUND ART

A fluoropolyoxyalkylene compound, particularly a perfluoropolyoxyalkylene compound is widely used as a lubricant, an intermediate for various polymers, or the like, and its applications have expanded further. A perfluoropolyoxyalkylene peroxide compound is known as a raw material of a perfluoropolyoxyalkylene compound, and decomposing and reducing a perfluoropolyoxyalkylene peroxide compound can provide a perfluoropolyoxyalkylene compound. As a method for producing a perfluoropolyoxyalkylene peroxide compound, for example, a method involving reacting tetrafluoroethylene with oxygen is known. Typically, this reaction is performed by reacting tetrafluoroethylene with oxygen under ultraviolet irradiation (Patent Literature 1).

CITATION LIST

Patent Literature

Patent Literature 1: Japanese Patent Laid-Open No. 09-227507

SUMMARY OF INVENTION

Technical Problem

As the applications of a perfluoropolyoxyalkylene compound expand, a situation where a perfluoropolyoxyalkylene compound having a particular molecular weight is required occurs. When a perfluoropolyoxyalkylene peroxide compound is decomposed and reduced to obtain a perfluoropolyoxyalkylene compound, a certain amount of a perfluoropolyoxyalkylene compound having an unintended molecular weight is produced. Therefore, it cannot be said that the yield of a perfluoropolyoxyalkylene compound having a target molecular weight is sufficient.

The present inventors have studied in order to solve the above problem, and as a result considered that when it is possible to oxidize a fluoropolyoxyalkylene compound having an unintended molecular weight, particularly a high molecular weight, again to form a fluoropolyoxyalkylene peroxide compound and decompose and reduce the resultant again, the yield of a fluoropolyoxyalkylene compound having a target molecular weight can be increased. Therefore, it is an object of the present invention to oxidize a fluoropolyoxyalkylene compound to obtain a fluoropolyoxyalkylene peroxide compound.

Solution to Problem

The present inventors have studied diligently and as a result found that treating a fluoropolyoxyalkylene compound in the presence of an oxygen source can provide a fluoropolyoxyalkylene peroxide compound, and arrived at the present invention.

The first aspect of the present invention provides a method for producing a fluoropolyoxyalkylene peroxide compound comprising one or more —$CF_2OOCF_2$— units, comprising treating a fluoropolyoxyalkylene compound comprising two or more —$CF_2O$— units in the presence of an oxygen source.

The second aspect of the present invention provides a fluoropolyoxyalkylene peroxide compound comprising active oxygen only as a —$CF_2OOCF_2$— unit.

Advantageous Effects of Invention

According to the present invention, treating a fluoropolyoxyalkylene compound in the presence of an oxygen source can convert the fluoropolyoxyalkylene compound into a fluoropolyoxyalkylene peroxide compound.

DESCRIPTION OF EMBODIMENTS

The production method of the present invention will be described in detail below.

In the fluoropolyoxyalkylene compound used in the production method of the present invention, at least part of a polyoxyalkylene main chain is substituted by fluorine, and the fluoropolyoxyalkylene compound comprises two or more —$CF_2O$— units. Preferably, the fluoropolyoxyalkylene compound is a perfluoropolyoxyalkylene compound, that is, the polyoxyalkylene main chain is fully substituted by fluorine. The groups bonded to the ends of the polyoxyalkylene main chain need not necessarily be substituted by fluorine and may be, for example, unsubstituted or substituted by chlorine or the like.

In one embodiment, the fluoropolyoxyalkylene main chain is represented by —$(C_{n'}F_{2n'}O)_{m'}$—.

In the above formula, n' can each independently be an integer of 1 or more and 6 or less, preferably an integer of 1 to 4, for example, 1 or 2, or 1, 2, or 3, for each unit in parentheses with m'.

m' can be an integer of 2 or more, preferably an integer of 2 or more and 3000 or less, and more preferably an integer of 20 to 2000.

The fluoropolyoxyalkylene main chain comprises two or more —$CF_2O$— units. The carbon atoms of such —$CF_2O$— units are bonded to the oxygen atoms of adjacent units unless they are at the ends of the main chain.

The groups bonded to the ends of the fluoropolyoxyalkylene main chain are not limited and can be preferably $R^3$ and $R^4$ described below.

In one embodiment, the fluoropolyoxyalkylene compound is a perfluoropolyoxyalkylene compound of formula (II):

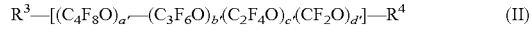

$$R^3—[(C_4F_8O)_{a'}—(C_3F_6O)_{b'}—(C_2F_4O)_{c'}—(CF_2O)_{d'}]—R^4 \quad (II)$$

In the formula, $R^3$ is a hydrogen atom, a fluorine atom, —$C_yF_{2y}CR^7{}_3$, —$C_yF_{2y}$—$COOCR^8{}_3$, —$C_yF_{2y}$—COOH, or —COF. $R^3$ is preferably a fluorine atom, —$C_yF_{2y}CR^7{}_3$, —$C_yF_{2y}$—$COOCR^8$, or —$C_yF_{2y}$—COOH, more preferably —$C_yF_{2y}CR^7{}_3$, —$C_yF_{2y}$—$COOCR^8$, or —$C_yF_{2y}$—COOH, further preferably —$C_yF_{2y}$—$COOCR^8$ or —$C_yF_{2y}$—COOH, and still more preferably —$C_yF_{2y}$—$COOCR^8$.

In the formula, $R^4$ is —$C_yF_{2y}CR^7{}_3$, —$C_yF_{2y}$—$COOCR^8{}_3$, —$C_yF_{2y}$—COOH, or —COF. $R^4$ is preferably —$C_yF_{2y}CR^7{}_3$, —$C_yF_{2y}$—$COOCR^8$, or —$C_yF_{2y}$—COOH, more preferably —$C_yF_{2y}$—$COOCR^8$ or —$C_yF_{2y}$—COOH, and further preferably —$C_yF_{2y}$—$COOCR^8$.

The above $R^7$ is each independently a fluorine atom, a chlorine atom, or a hydrogen atom. $R^7$ is each independently preferably a fluorine atom or a hydrogen atom, more preferably a hydrogen atom.

The above $R^8$ is each independently a fluorine atom or a hydrogen atom, preferably a hydrogen atom. In one embodiment, two of three $R^8$ present in each unit are fluorine atoms, and one is a hydrogen atom. In another embodiment, three $R^8$ present in each unit are all fluorine atoms.

The above y can be independently an integer of 0 or more and 16 or less, preferably an integer of 0 to 6, and more preferably an integer of 0 to 3, for example, 0, 1, or 2, or 0 or 1, for each unit.

In a preferred embodiment, $R^3$ can be —$C_yF_{2y}$—$COOCH_3$ or —$C_yF_{2y}$—$COOCHF_2$, preferably —$C_yF_{2y}$—$COOCH_3$. In such an embodiment, y can be preferably 0 or 1, more preferably 0.

In a preferred embodiment, $R^4$ can be —$C_yF_{2y}$—$COOCH_3$ or —$C_yF_{2y}$—$COOCHF_2$, preferably —$C_yF_{2y}$—$COOCH_3$. In such an embodiment, y is preferably 1 or 2.

In the formula, a', b', and c' can each independently be an integer of 0 or 1 or more, preferably an integer of 0 to 1000, for example, an integer of 5 or more, 10 or more, or 20 or more and 800 or less, 600 or less, 300 or less, or 200 or less.

In the formula, d' can be an integer of 2 or more, preferably an integer of 2 to 1000, for example, an integer of 5 or more, 10 or more, or 20 or more and 800 or less, 600 or less, 300 or less, or 200 or less.

The sum of the above a', b', c', and d' can be preferably an integer of 2 or more and 2000 or less, more preferably an integer of 2 or more and 1500 or less, for example, an integer of 10 or more, 30 or more, or 50 or more and 1000 or less, 800 or less, or 600 or less.

In the formula, the order of the repeating units in parentheses with subscript a', b', c', or d' is arbitrary in the formula.

Among the repeating units, —$(C_4F_8O)$— may be, for example, any of —$(CF_2CF_2CF_2CF_2O)$—, —$(CF(CF_3)CF_2CF_2O)$—, —$(CF_2CF(CF_3)CF_2O)$—, —$(CF_2CF_2CF(CF_3)O)$—, —$(C(CF_3)_2CF_2O)$—, —$(CF_2C(CF_3)_2O)$—, —$(CF(CF_3)CF(CF_3)O)$—, —$(CF(C_2F_5)CF_2O)$—, and —$(CF_2CF(C_2F_5)O)$— but is preferably —$(CF_2CF_2CF_2CF_2O)$—. —$(C_3F_6O)$— may be, for example, any of —$(CF_2CF_2CF_2O)$—, —$(CF(CF_3)CF_2O)$—, and —$(CF_2CF(CF_3)O)$— but is preferably —$(CF_2CF_2CF_2O)$—. —$(C_2F_4O)$— may be, for example, any of —$(CF_2CF_2O)$— and —$(CF(CF_3)O)$— but is preferably —$(CF_2CF_2O)$—.

In one embodiment, a' and b' can each independently be an integer of 0 or more and 100 or less, preferably an integer of 0 to 50, and c' and d' can each independently be an integer of 2 or more and 1000 or less, preferably an integer of 10 to 500, for example, an integer of 20 to 300.

In another embodiment, a' and b' can each be 0, and c' and d' can each independently be an integer of 2 or more and 1000 or less, preferably an integer of 10 to 500, for example, an integer of 20 to 300.

In a preferred embodiment, the fluoropolyoxyalkylene compound is a compound of formula (II'):

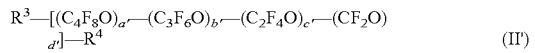

(II')

wherein
$R^3$ is —$C_yF_{2y}$—$COOCR^8_3$ or —$C_yF_{2y}$—COOH, preferably —$C_yF_{2y}$—$COOCR^8_3$, $R^4$ is —$C_yF_{2y}$—$COOCR^8_3$ or —$C_yF_{2y}$—COOH, preferably —$C_yF_{2y}$—$COOCR^8_3$, $R^8$ is each independently a hydrogen atom, y is independently 0, 1, or 2 for each unit, a' and b' are each independently an integer of 0 or more and 100 or less, c' and d' are each independently an integer of 2 or more and 1000 or less, and the order of the repeating units in parentheses with subscript a', b', c', or d' is arbitrary in the formula.

In one embodiment, the number average molecular weight of the above fluoropolyoxyalkylene compound is not limited and can be, for example, 3,000 or more, preferably 5,000 or more, for example, 10,000 or more, 15,000 or more, or 30,000 or more. The upper limit of the number average molecular weight of the fluoropolyoxyalkylene compound is not limited and can be, for example, 150,000 or less, 100,000 or less, or 50,000 or less.

In the present invention, the "number average molecular weight" is measured by GPC (gel permeation chromatography) analysis unless otherwise specified.

The oxygen source used in the present invention is not limited, and examples thereof include oxygen gas ($O_2$), CO, carbonic acid gases (for example, $Cs_2CO_3$), carboxylic acids, carboxylate esters, $SiO_2$, $H_2O$, $CO_2$, $O_3$, or hypofluorides (for example, $CF_3OF$). As the oxygen source, only one oxygen source may be used, but two or more oxygen sources may be used.

In one embodiment, the oxygen source can be a carboxylic acid or a carboxylate ester, preferably a carboxylate ester.

The carboxylic acid or the carboxylate ester as the above oxygen source is preferably one in which the main chain is stable in the steps in the production method of the present invention. The main chain of the above carboxylic acid or carboxylate ester can be preferably an alkylene chain optionally substituted by fluorine or a polyoxyalkylene chain optionally substituted by fluorine, more preferably a perfluoroalkylene chain or a perfluoropolyoxyalkylene chain.

In a preferred embodiment, the carboxylic acid or the carboxylate ester as the above oxygen source is, for example, a compound of the following formula:

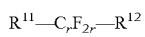

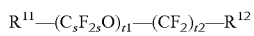

wherein
$R^{11}$ is each independently —COOH or —$COOR^{13}$, $R^{12}$ is each independently a fluorine atom, —COOH, or —$COOR^{13}$, $R^{13}$ is a lower alkyl group, preferably a $C_{1-3}$ alkyl group, more preferably a methyl group or an ethyl group, and further preferably a methyl group, r is an integer of 1 or more and 1000 or less, preferably an integer of 2 to 100, and more preferably an integer of 5 to 50, s is an integer of 1 or more and 6 or less, preferably an integer of 1 to 4, for example, 1 or 2, or 1,2, or 3, t1 is an integer of 1 or more and 1000 or less, preferably an integer of 1 to 100, and more preferably an integer of 1 to 50, t2 is an integer of 0 or more and 1000 or less, preferably an integer of 0 to 100, and more preferably an integer of 0 to 50, and the order of the repeating units in parentheses with subscript t1 or t2 is arbitrary in the formula.

In another preferred embodiment, the carboxylic acid or the carboxylate ester as the above oxygen source can be a compound of the above formula (II) wherein one or both of $R^3$ and $R^4$ are each independently —$C_yF_{2y}$—COOCR$^8{}_3$ or —$C_yF_{2y}$—COOH.

When the oxygen source is a gas, for example, oxygen gas, it may be used as it is, and it may be mixed with an inert gas (for example, nitrogen or a rare gas, for example, argon) and used. When the oxygen source is mixed with an inert gas, the concentration of the oxygen source is not limited and can be, for example, 1% by volume or more and 80% by volume or less, preferably 5 to 50% by volume, for example, 10 to 30% by volume.

The amount of the oxygen source used (in terms of $O_2$) based on the fluoropolyoxyalkylene compound can be preferably 0.001 mol or more and 50 mol or less, more preferably 0.01 to 10 mol, and further preferably 0.05 to 5.0 mol, for example, 0.1 to 5.0 mol, 0.001 to 1.5 mol, 0.001 to 1.0 mol, 0.01 to 1.0, or 0.01 to 0.5 mol, based on 1 mol of the perfluoropolyoxyalkylene compound.

In the production method of the present invention, the above fluoropolyoxyalkylene compound is treated in the presence of the above oxygen source. By such treatment, the fluoropolyoxyalkylene compound reacts with oxygen, is oxidized, and forms a peroxide. Such treatment can be performed by mixing the fluoropolyoxyalkylene compound and the above oxygen source and may be performed batchwise or continuously.

Preferably, the above treatment is performed in the presence of a fluorine source in addition to an oxygen source, that is, in the presence of an oxygen source and a fluorine source. Such treatment can be performed by mixing the fluoropolyoxyalkylene compound, the oxygen source, and the fluorine source and may be performed batchwise or continuously.

The above fluorine source is not limited and is fluorine gas ($F_2$) or $R^{21}$—OF wherein $R^{21}$ is a perfluoroalkyl group having 1 to 6 carbon atoms. As the fluorine source, only one fluorine source may be used, but two or more fluorine sources may be used. Preferably, the fluorine source is $F_2$.

Fluorine gas may be used as it is, and fluorine gas may be mixed with an inert gas (for example, nitrogen or a rare gas, for example, argon) and used. When fluorine gas is mixed with an inert gas, the concentration of fluorine gas is not limited and can be, for example, 1% by volume or more and 80% by volume or less, preferably 5 to 50% by volume, for example, 10 to 30% by volume.

The amount of the fluorine source used (in terms of $F_2$) based on the fluoropolyoxyalkylene compound is not limited and can be a large excess amount. For example, the amount of the fluorine source used (in terms of $F_2$) can be 100 times or more or 50 times or more based on 1 mol of the perfluoropolyoxyalkylene compound.

In a preferred embodiment, in the combination of the above oxygen source and fluorine source, the oxygen source is a carboxylate ester and the fluorine source is fluorine gas.

In a preferred embodiment, the amount of the fluorine source used (in terms of $F_2$) can be 100 times or more, and the amount of the oxygen source used (in terms of $O_2$) can be 0.001 mol or more and 5.0 mol or less, preferably 0.01 to 3.0 mol, and more preferably 0.05 to 2.0 mol, based on 1 mol of the perfluoropolyoxyalkylene compound.

The treatment temperature is not limited as long as it is a temperature at which the reaction proceeds, and the product is stable. The treatment temperature can be, for example, 50° C. or more and 200° C. or less, preferably 80 to 180° C., and more preferably 100 to 150° C.

The treatment pressure is not limited as long as the reaction proceeds. The treatment pressure can be, for example, 0.1 MPa or more and 1.0 MPa or less, preferably 0.1 to 0.5 MPa.

The treatment time can change according to the compound used, the type of reaction container, and the like and can be, for example, 10 minutes or more and 24 hours or less, preferably 1 to 12 hours, for example, 2 to 10 hours.

In the reaction of the fluoropolyoxyalkylene compound and the oxygen source, preferably the fluoropolyoxyalkylene compound, the oxygen source, and the fluorine source, in the present invention, active oxygen is selectively introduced into a portion adjacent to the —$CF_2O$— units in the fluoropolyoxyalkylene compound to obtain a fluoropolyoxyalkylene peroxide compound comprising a —$CF_2OOCF_2O$— unit.

Therefore, the present invention also provides a fluoropolyoxyalkylene peroxide compound comprising active oxygen mainly as a —$CF_2OOCF_2O$— unit. The carbon atom at an end of such a —$CF_2OOCF_2O$— unit is bonded to an oxygen atom of an adjacent unit unless it is at an end of the main chain.

Preferably 90 mol % or more, more preferably 95 mol % or more, further preferably 98 mol % or more, still more preferably 99 mol % or more, particularly preferably 99.5 mol % or more, and most preferably substantially 100 mol % of the active oxygen in the above fluoropolyoxyalkylene peroxide compound is present as a —$CF_2OOCF_2O$— unit.

The above fluoropolyoxyalkylene peroxide compound can comprise, for example, as —$CF_2CF_2OOCF_2CF_2O$—, —$CF_2OOCF_2CF_2O$—, or —$CF_2CF_2OOCF_2O$—, active oxygen other than the active oxygen present as a —$CF_2OOCF_2O$— unit.

In a preferred embodiment, the present invention also provides a fluoropolyoxyalkylene peroxide compound comprising active oxygen only as a —$CF_2OOCF_2O$— unit. Preferably, the fluoropolyoxyalkylene peroxide compound is a perfluoropolyoxyalkylene peroxide compound. The carbon atom at an end of such a —$CF_2OOCF_2O$— unit is bonded to an oxygen atom of an adjacent unit unless it is at an end of the main chain.

In one embodiment, the fluoropolyoxyalkylene peroxide main chain is represented by —$(C_nF_{2n}O)_m$—$(CF_2OOCF_2jO)_p$—.

In the above formula, n can each independently be an integer of 1 or more and 6 or less, preferably an integer of 1 to 4, for example, 1 or 2, or 1, 2, or 3, for each unit in parentheses with m.

m can be an integer of 2 or more, preferably an integer of 2 to 3000, and more preferably an integer of 20 to 2000.

p can be an integer of 1 or more and 250 or less, preferably an integer of 5 to 250, for example, an integer of 10 or more or 20 or more and 150 or less, 100 or less, 50 or less, or 40 or less.

The groups bonded to the ends of the fluoropolyoxyalkylene peroxide main chain are not limited and can be preferably $R^1$ and $R^2$ described below.

In one embodiment, the fluoropolyoxyalkylene peroxide compound of the present invention is a compound of formula (I):

$$R^1—[(C_4F_8O)_a—(C_3F_6O)_b—(C_2F_4O)_c—(CF_2O)_d—(CF_2OOCF_2O)_p]—R^2 \quad (I)$$

In the formula, $R^1$ is a hydrogen atom, a fluorine atom, —$C_xF_{2x}CR^5{}_3$, —$C_xF_{2x}$—COOCR$^6{}_3$, —$C_xF_{2x}$—COOH, or —COF. Preferably, $R^1$ is a fluorine atom or —$C_xF_{2x}CR^5{}_3$.

In the formula, $R^2$ is $-C_xF_{2x}CR^5_3$, $-C_xF_{2x}-COOCR^6_3$, $-C_xF_{2x}-COOH$, or $-COF$. Preferably, $R^2$ is $-C_xF_{2x}CR^5_3$.

The above $R^5$ is each independently a fluorine atom, a chlorine atom, or a hydrogen atom. $R^5$ is each independently preferably a fluorine atom or a hydrogen atom, more preferably a fluorine atom. In one embodiment, two of three $R^5$ present in each unit are fluorine atoms, and one is a hydrogen atom. In another embodiment, three $R^5$ present in each unit are all fluorine atoms.

The above $R^6$ is each independently a fluorine atom or a hydrogen atom, preferably a fluorine atom. In one embodiment, two of three $R^6$ present in each unit are fluorine atoms, and one is a hydrogen atom. In another embodiment, three $R^6$ present in each unit are all fluorine atoms.

The above x can be independently an integer of 0 or more and 16 or less, preferably an integer of 0 to 6, and more preferably an integer of 0 to 3, for example, 0, 1, or 2, or 0 or 1, for each unit.

In a preferred embodiment, $R^1$ is a fluorine atom, $-C_xF_{2x}CF_3$, or $-C_xF_{2x}CHF_2$, preferably a fluorine atom or $-C_xF_{2x}CF_3$. In such an embodiment, x can be preferably 0 or 1, more preferably 0.

In a preferred embodiment, $R^2$ is $-C_xF_{2x}CF_3$ or $-C_xF_{2x}CHF_2$. In such an embodiment, x is preferably 1 or 2.

In the formula, a, b, c, and d can each independently be an integer of 0 or 1 or more, preferably an integer of 0 to 1000, for example, an integer of 5 or more, 10 or more, or 20 or more and 800 or less, 600 or less, 300 or less, or 200 or less.

The sum of the above a, b, c, and d can be preferably an integer of 2 or more and 2000 or less, more preferably an integer of 2 to 1500, for example, an integer of 10 or more, 30 or more, or 50 or more and 1000 or less, 800 or less, or 600 or less.

p has the same meaning as above and is an integer of 1 or more and 250 or less. Preferably, p can be an integer of 5 or more and 250 or less, for example, an integer of 10 or more or 20 or more and 150 or less, 100 or less, 50 or less, or 40 or less.

In the formula, the order of the repeating units in parentheses with subscript a, b, c, d, or p is arbitrary in the formula.

Among the repeating units, $-(C_4F_8O)-$ may be, for example, any of $-(CF_2CF_2CF_2CF_2O)-$, $-(CF(CF_3)CF_2CF_2O)-$, $-(CF_2CF(CF_3)CF_2O)-$, $-(CF_2CF_2CF(CF_3)O)-$, $-(C(CF_3)_2CF_2O)-$, $-(CF_2C(CF_3)_2O)-$, $-(CF(CF_3)CF(CF_3)O)-$, $-(CF(C_2F_5)CF_2O)-$, and $-(CF_2CF(C_2F_5)O)-$ but is preferably $-(CF_2CF_2CF_2CF_2O)-$. $-(C_3F_6O)-$ may be, for example, any of $-(CF_2CF_2CF_2O)-$, $-(CF(CF_3)CF_2O)-$, and $-(CF_2CF(CF_3)O)-$ but is preferably $-(CF_2CF_2CF_2O)-$. $-(C_2F_4O)-$ may be, for example, any of $-(CF_2CF_2O)-$ and $-(CF(CF_3)O)-$ but is preferably $-(CF_2CF_2O)-$.

In one embodiment, a and b can each independently be an integer of 0 or more and 100 or less, preferably an integer of 0 or more and 50 or less, and c and d can each independently be an integer of 1 or more and 1000 or less, preferably an integer of 10 or more and 500 or less, for example, an integer of 20 or more and 300 or less.

In another embodiment, a and b can each be 0, and c and d can each independently be an integer of 2 or more and 1000 or less, preferably an integer of 10 or more and 500 or less, for example, an integer of 20 or more and 300 or less.

In a preferred embodiment, the fluoropolyoxyalkylene peroxide compound is a compound of formula (I'):

$$R^1-[(C_4F_8O)_a-(C_3F_6O)_b-(C_2F_4O)_c-(CF_2O)_d-(CF_2OOCF_2O)_p]-R^2 \quad (I')$$

wherein
$R^1$ is a fluorine atom or $-C_xF_{2x}CR^5_3$,
$R^2$ is $-C_xF_{2x}CR^5_3$,
$R^5$ is each independently a fluorine atom,
x is independently 0, 1, or 2 for each unit,
a and b are each independently an integer of 0 or more and 100 or less,
c and d are each independently an integer of 1 or more and 1000 or less,
p is an integer of 1 or more and 250 or less, and
the order of the repeating units in parentheses with subscript a, b, c, d, or p is arbitrary in the formula.

In one embodiment, the number average molecular weight of the above fluoropolyoxyalkylene peroxide compound is not limited and can be, for example, 3,000 or more, preferably 5,000 or more, for example, 10,000 or more, 15,000 or more, or 30,000 or more. The upper limit of the number average molecular weight of the fluoropolyoxyalkylene peroxide compound is not limited and can be, for example, 150,000 or less, 100,000 or less, or 50,000 or less.

In one embodiment, the PO value of the fluoropolyoxyalkylene peroxide compound of the present invention can be preferably 5.0 or less, more preferably 3.0 or less, for example, 2.0 or less, 1.0 or less, 0.5 or less, or 0.1 or less. The PO value can be preferably 0.001 or more, more preferably 0.01 or more, for example, 0.05 or more, 0.1 or more, 0.5 or more, or 1.0 or more. The PO value means the mass of active oxygen (one of oxygens forming $-O-O-$) contained per 100 g of the compound.

In the present invention, the PO value is measured by $^{19}$F-NMR analysis.

Decomposing and reducing the fluoropolyoxyalkylene peroxide compound of formula (I) obtained by the production method of the present invention can provide a fluoropolyoxyalkylene compound having a lower molecular weight than the fluoropolyoxyalkylene compound of formula (II) used as the raw material. In other words, using the method of the present invention can lower the molecular weight of a perfluoropolyoxyalkylene compound. In addition, the $-CF_2O-CF_2O-$ unit of a fluoropolyoxyalkylene compound is oxidized and forms the $-CF_2OOCF_2O-$ unit of a fluoropolyoxyalkylene peroxide compound, and cutting this portion provides a new fluoropolyoxyalkylene compound, and therefore a fluoropolyoxyalkylene compound having fewer methylene oxide chains than the fluoropolyoxyalkylene compound used as the raw material can be obtained. In other words, a compound of formula (II) having a larger c'/d' ratio can be obtained.

In a conventional method, specifically a method involving reacting tetrafluoroethylene with oxygen to obtain a perfluoropolyoxyalkylene peroxide compound, and decomposing and reducing this to obtain a perfluoropolyoxyalkylene compound, a perfluoropolyoxyalkylene compound having a molecular weight larger than the intended molecular weight is recognized as a by-product. According to the method of the present invention, it is possible to oxidize such a perfluoropolyoxyalkylene compound as a by-product again to form a perfluoropolyoxyalkylene peroxide compound, and then decompose and reduce the perfluoropolyoxyalkylene peroxide compound to obtain a perfluoropolyoxyalkylene compound having a lower molecular weight, and therefore the yield improves.

In addition, in the method of the present invention, the reaction is mild compared with the method for producing a perfluoropolyoxyalkylene peroxide compound in which tetrafluoroethylene is reacted with oxygen, and therefore the method of the present invention is advantageous in that the control of the reaction is easy.

Further, the reaction of the present invention does not require light irradiation for the synthesis of the peroxide, and therefore it is not necessary to make the reaction container transparent, and the reaction of the present invention is advantageous in the selection of the reaction container.

The present invention is not limited and discloses the following embodiments.

Embodiment 1. A method for producing a fluoropolyoxyalkylene peroxide compound comprising one or more —$CF_2OOCF_2O$— units, comprising treating a fluoropolyoxyalkylene compound comprising two or more —$CF_2O$— units in the presence of an oxygen source.

Embodiment 2. The method according to embodiment 1, wherein the fluoropolyoxyalkylene compound comprising two or more —$CF_2O$— units is treated in the presence of a fluorine source and an oxygen source.

Embodiment 3. The method according to embodiment 1 or 2, wherein the fluoropolyoxyalkylene peroxide compound is a perfluoropolyoxyalkylene peroxide compound of formula (I):

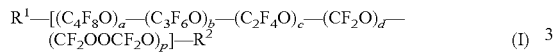  (I)

wherein $R^1$ is a hydrogen atom, a fluorine atom, —$C_xF_{2x}CR^5{}_3$, —$C_xF_{2x}$—$COOCR^6{}_3$, —$C_xF_{2x}$—COOH, or —COF, $R^2$ is —$C_xF_{2x}CR^5{}_3$, —$C_xF_{2x}$—$COOCR^6{}_3$, —$C_xF_{2x}$—COOH, or —COF, $R^5$ is each independently a fluorine atom, a chlorine atom, or a hydrogen atom, $R^6$ is each independently a fluorine atom or a hydrogen atom, x is independently an integer of 0 or more and 16 or less for each unit, a, b, c, and d are each independently an integer of 0 or 1 or more, a sum of a, b, c, and d is 1 or more, p is an integer of 1 or more and 250 or less, and an order of repeating units in parentheses with subscript a, b, c, d, or p is arbitrary in the formula, and the fluoropolyoxyalkylene compound is a perfluoropolyoxyalkylene compound of formula (II):

  (II)

wherein $R^3$ is a hydrogen atom, a fluorine atom, —$C_yF_{2y}CR^7{}_3$, —$C_yF_{2y}$—$COOCR^8{}_3$, —$C_yF_{2y}$—COOH, or —COF, $R^4$ is —$C_yF_{2y}CR^7{}_3$, —$C_yF_{2y}$—$COOCR^8{}_3$, —$C_yF_{2y}$—COOH, or —COF $R^7$ is each independently a fluorine atom, a chlorine atom, or a hydrogen atom, $R^8$ is each independently a fluorine atom or a hydrogen atom, y is independently an integer of 0 to 16 for each unit, a', b', and c' are each independently an integer of 0 or 1 or more, d' is an integer of 2 or more, and an order of repeating units in parentheses with subscript a', b', c', or d' is arbitrary in the formula.

Embodiment 4. The method according to embodiment 3, wherein the perfluoropolyoxyalkylene peroxide compound is a compound of formula (I)

wherein a and b are each independently an integer of 0 or more and 100 or less, and c and d are each independently an integer of 1 or more and 1000 or less, and the perfluoropolyoxyalkylene compound is a compound of formula (II)

wherein a' and b' are each independently an integer of 0 or more and 100 or less, and c' and d' are each independently an integer of 1 or more and 1000 or less.

Embodiment 5. The method according to any one of embodiments 1 to 4, wherein the oxygen source is $O_2$, CO, a carbonate salt, a carboxylic acid, or a carboxylate ester.

Embodiment 6. The method according to any one of embodiments 1 to 5, wherein the oxygen source is a carboxylic acid or a carboxylate ester.

Embodiment 7. The method according to any one of embodiments 3 to 6, wherein a perfluoropolyoxyalkylene compound of formula (II) wherein $R^3$ is —$C_yF_{2y}$—$COOCH_3$ or —$C_yF_{2y}$—COOH, and/or $R^4$ is —$C_yF_{2y}$—$COOCH_3$ or —$C_yF_{2y}$—COOH is used as the oxygen source.

Embodiment 8. A fluoropolyoxyalkylene peroxide compound comprising active oxygen only as a —$CF_2OOCF_2O$— unit.

Embodiment 9. The fluoropolyoxyalkylene peroxide compound according to embodiment 8, of formula (I):

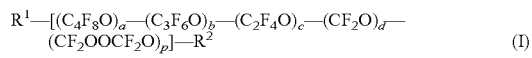  (I)

wherein $R^1$ is a hydrogen atom, a fluorine atom, —$C_xF_{2x}CR^5{}_3$, —$C_xF_{2x}$—$COOCR^6{}_3$, —$C_xF_{2x}$—COOH, or —COF, $R^2$ is —$C_xF_{2x}CR^5{}_3$, —$C_xF_{2x}$—$COOCR^6{}_3$, —$C_xF_{2x}$—COOH, or —COF, $R^5$ is each independently a fluorine atom, a chlorine atom, or a hydrogen atom, $R^6$ is each independently a fluorine atom or a hydrogen atom, x is independently an integer of 0 to 16 for each unit, a, b, c, and d are each independently an integer of 0 or 1 or more, a sum of a, b, c, and d is at least 1, p is an integer of 1 or more and 250 or less, and an order of repeating units in parentheses with subscript a, b, c, d, or p is arbitrary in the formula.

Embodiment 10. The fluoropolyoxyalkylene peroxide compound according to embodiment 9, being a compound of formula (I)

wherein a and b are each independently an integer of 0 or more and 100 or less, c and d are each independently an integer of 1 or more and 1000 or less, and p is an integer of 1 or more and 250 or less.

EXAMPLES

Example 1

The following compound (1a-1) (70.8 g) having a number average molecular weight of 4519 was placed in a 100 mL three-necked round bottom flask, the internal temperature of the reactor was increased to 140° C., and then a 15.5 vol % $F_2/N_2$ mixed gas was supplied at 40 ml/min for 8 hours. After the reaction, the solution was recovered to obtain the following compound (1a-2) (69.1 g). The weight (PO value) of active oxygen per 100 g of the product calculated from $^{19}$F-NMR for the compound (1a-2) was 0.02.

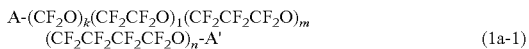
(1a-1)

(A and A' are each any of —CF$_2$Cl, —CF$_3$, —CF$_2$CF$_3$, or COOCH$_3$, and their respective abundance ratios are 2%, 1%, 1%, and 96%.)

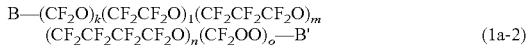
(1a-2)

(B and B' are each any of —CF$_2$Cl, —CF$_3$, —CF$_2$CF$_3$, COOCHF$_2$, or COOCF$_3$, and their respective abundance ratios are 2%, 60%, 1%, 29%, and 8%.)

Example 2

Diethylene glycol dimethyl ether (67.0 g) and NaBH$_4$ (1.24 g) were placed in a 100 ml three-necked round bottom flask equipped with a reflux condenser and a dropping funnel, and while the mixture was stirred, the compound (1a-2) (61.2 g) obtained in Example 1 was dropped over 10 minutes. Then, the internal temperature of the reactor was increased to 120° C. under reflux at 20° C., and the mixture was stirred for 6 hours. After the heating and stirring, 3 N hydrochloric acid, acetone, and perfluorohexane were added to the reaction liquid to wash and separate the reaction liquid to recover the product three times to obtain the following compound (1a-3) (60.3 g). The number average molecular weight of the compound (1a-3) was 4030.

(1a-3)

(C and C' are each any of —CF$_2$Cl, —CF$_3$, —CF$_2$CF$_3$, or CH$_2$OH, and their respective abundance ratios are 2%, 60%, 1%, and 37%.)

Example 3

The following compound (2a-1) (27.3 g) having a number average molecular weight of 4519 was placed in a 100 mL three-necked round bottom flask, the internal temperature of the reactor was increased to 140° C., and then a 1.5 wt % F$_2$/N$_2$ mixed gas was supplied at 20 ml/min for 1 hour and 30 minutes. After the reaction, the solution was recovered to obtain the following compound (2a-2) (26.8 g). The weight (PO value) of active oxygen per 100 g of the product calculated from $^{19}$F-NMR for the compound (2a-2) was 0.01.

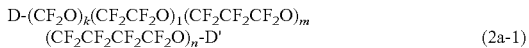
(2a-1)

(D and D' are each any of —CF$_2$Cl, —CF$_3$, —CF$_2$CF$_3$, or —COOH, and their respective abundance ratios are 2%, 1%, 1%, and 96%.)

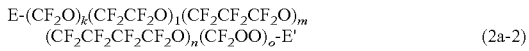
(2a-2)

(E and E' are each any of —CF$_2$Cl, —CF$_3$, —CF$_2$CF$_3$, or —COOH, and their respective abundance ratios are 2%, 55%, 1%, and 42%.)

Example 4

The following compound (3a-1) (40.0 g) and compound (3a-2) (40.0 g) having a number average molecular weight of 4183 were placed in a 100 mL three-necked round bottom flask, the internal temperature of the reactor was increased to 140° C., and then a 1.5 wt % F$_2$/N$_2$ mixed gas was supplied at 55 ml/min for 14 hours. The result of analyzing the solution after the reaction demonstrates that it was a mixture of the following compound (3a-1)' and compound (3a-2)'. The weight (PO value) of active oxygen per 100 g of the product calculated from $^{19}$F-NMR for the compound (3a-1)' was 0.098.

(3a-1)

(F and F' are each any of —CF$_2$Cl, —CF$_3$, or —CF$_2$CF$_3$, and their respective abundance ratios are 1%, 95%, and 4%.)

(3a-2)

(G and G' are each any of —CF$_2$CF$_2$CF$_3$, —CF$_2$CF$_3$, or CF$_2$CF$_2$COOCH$_3$, and their respective abundance ratios are 50%, 4%, and 46%.)

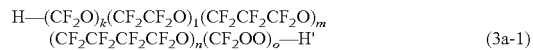
(3a-1)

(F and F' are each any of —CF$_2$Cl, —CF$_3$, or —CF$_2$CF$_3$, and their respective abundance ratios are 1%, 95%, and 4%.)

(3a-2)'

(I and I' are each any of —CF$_2$CF$_2$CF$_3$, —CF$_2$CF$_3$, —CF$_2$CF$_2$COOCH$_3$, CF$_2$CF$_2$COOCF$_2$H, or CF$_2$CF$_2$COOCF$_3$, and their respective abundance ratios are 48%, 26%, 3%, 14%, and 9%.)

INDUSTRIAL APPLICABILITY

According to the present invention, a perfluoropolyoxyalkylene peroxide compound can be preferably produced from a perfluoropolyoxyalkylene compound.

The invention claimed is:

1. A method for producing a fluoropolyoxyalkylene peroxide compound comprising one or more —CF$_2$OOCF$_2$O— units,
comprising treating a fluoropolyoxyalkylene compound comprising two or more —CF$_2$O— units in the presence of an oxygen source.

2. The method according to claim 1, wherein the fluoropolyoxyalkylene compound comprising two or more —CF$_2$O— units is treated in the presence of a fluorine source and an oxygen source.

3. The method according to claim 1, wherein the fluoropolyoxyalkylene peroxide compound is a perfluoropolyoxyalkylene peroxide compound of formula (I):

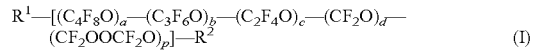
(I)

wherein
R$^1$ is a hydrogen atom, a fluorine atom, —C$_x$F$_{2x}$CR$^5_3$, —C$_x$F$_{2x}$—COOCR$^6_3$, —C$_x$F$_{2x}$—COOH, or —COF,
R$^2$ is —C$_x$F$_{2x}$CR$^5_3$, —C$_x$F$_{2x}$—COOCR$^6_3$, —C$_x$F$_{2x}$—COOH, or —COF,
R$^5$ is each independently a fluorine atom, a chlorine atom, or a hydrogen atom,
R$^6$ is each independently a fluorine atom or a hydrogen atom,
x is independently an integer of 0 or more and 16 or less for each unit,
a, b, c, and d are each independently an integer of 0 or 1 or more,
a sum of a, b, c, and d is 1 or more,
p is an integer of 1 or more and 250 or less, and an order of repeating units in parentheses with subscript a, b, c, d, or p is arbitrary in the formula, and the fluoropolyoxyalkylene compound is a perfluoropolyoxyalkylene compound of formula (II):

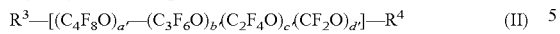   (II)

wherein
R$^3$ is a hydrogen atom, a fluorine atom, —C$_y$F$_{2y}$CR$^7_3$, —C$_y$F$_{2y}$—COOCR$^8_3$, —C$_y$F$_{2y}$—COOH, or —COF, R$^4$ is —C$_y$F$_{2y}$CR$^7_3$, —C$_y$F$_{2y}$—COOCR$^8_3$, —C$_y$F$_{2y}$—COOH, or —COF, R$^7$ is each independently a fluorine atom, a chlorine atom, or a hydrogen atom, R$^8$ is each independently a fluorine atom or a hydrogen atom, y is independently an integer of 0 to 16 for each unit, a', b', and c' are each independently an integer of 0 or 1 or more, d' is an integer of 2 or more, and an order of repeating units in parentheses with subscript a', b', c', or d' is arbitrary in the formula.

4. The method according to claim 3, wherein the perfluoropolyoxyalkylene peroxide compound is a compound of formula (I)

wherein a and b are each independently an integer of 0 or more and 100 or less, and c and d are each independently an integer of 1 or more and 1000 or less, and the perfluoropolyoxyalkylene compound is a compound of formula (II)

wherein a' and b' are each independently an integer of 0 or more and 100 or less, and c' and d' are each independently an integer of 1 or more and 1000 or less.

5. The method according to claim 1, wherein the oxygen source is O$_2$, CO, a carbonate salt, a carboxylic acid, or a carboxylate ester.

6. The method according to claim 1, wherein the oxygen source is a carboxylic acid or a carboxylate ester.

7. The method according to claim 3, wherein a perfluoropolyoxyalkylene compound of formula (II) wherein R$^3$ is —C$_y$F$_{2y}$—COOCH$_3$ or —C$_y$F$_{2y}$—COOH, and/or R$^4$ is —C$_y$F$_{2y}$—COOCH$_3$ or —C$_y$F$_{2y}$—COOH is used as the oxygen source.

8. A fluoropolyoxyalkylene peroxide compound comprising an active oxygen only as a —CF$_2$OOCF$_2$— unit.

9. The fluoropolyoxyalkylene peroxide compound according to claim 8 which is a compound of formula (I):

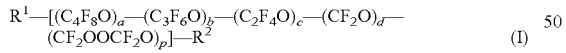   (I)

wherein
R$^1$ is a hydrogen atom, a fluorine atom, —C$_x$F$_{2x}$CR$^5_3$, —C$_x$F$_{2x}$—COOCR$^6_3$, —C$_x$F$_{2x}$—COOH, or —COF, R$^2$ is —C$_x$F$_{2x}$CR$^5_3$, —C$_x$F$_{2x}$—COOCR$^6_3$, —C$_x$F$_{2x}$—COOH, or —COF, R$^5$ is each independently a fluorine atom, a chlorine atom, or a hydrogen atom, R$^6$ is each independently a fluorine atom or a hydrogen atom, x is independently an integer of 0 to 16 for each unit, a, b, c, and d are each independently an integer of 0 or 1 or more, a sum of a, b, c, and d is 1 or more, p is an integer of 1 or more and 250 or less, and an order of repeating units in parentheses with subscript a, b, c, d, or p is arbitrary in the formula.

10. The fluoropolyoxyalkylene peroxide compound according to claim 9 which is a compound of formula (I) wherein a and b are each independently an integer of 0 or more and 100 or less, c and d are each independently an integer of 1 or more and 1000 or less, and p is an integer of 1 or more and 250 or less.

11. The method according to claim 2, wherein the fluoropolyoxyalkylene peroxide compound is a perfluoropolyoxyalkylene peroxide compound of formula (I):

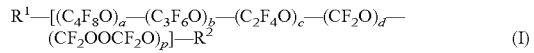   (I)

wherein
R$^1$ is a hydrogen atom, a fluorine atom, —C$_x$F$_{2x}$CR$^5_3$, —C$_x$F$_{2x}$—COOCR$^6_3$, —C$_x$F$_{2x}$—COOH, or —COF, R$^2$ is —C$_x$F$_{2x}$CR$^5_3$, —C$_x$F$_{2x}$—COOCR$^6_3$, —C$_x$F$_{2x}$—COOH, or —COF, R$^5$ is each independently a fluorine atom, a chlorine atom, or a hydrogen atom, R$^6$ is each independently a fluorine atom or a hydrogen atom, x is independently an integer of 0 or more and 16 or less for each unit, a, b, c, and d are each independently an integer of 0 or 1 or more, a sum of a, b, c, and d is 1 or more, p is an integer of 1 or more and 250 or less, and an order of repeating units in parentheses with subscript a, b, c, d, or p is arbitrary in the formula, and the fluoropolyoxyalkylene compound is a perfluoropolyoxyalkylene compound of formula (II):

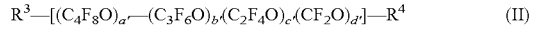   (II)

wherein
R$^3$ is a hydrogen atom, a fluorine atom, —C$_y$F$_{2y}$CR$^7_3$, —C$_y$F$_{2y}$—COOCR$^8_3$, —C$_y$F$_{2y}$—COOH, or —COF, R$^4$ is —C$_y$F$_{2y}$CR$^7_3$, —C$_y$F$_{2y}$—COOCR$^8_3$, —C$_y$F$_{2y}$—COOH, or —COF R$^7$ is each independently a fluorine atom, a chlorine atom, or a hydrogen atom, R$^8$ is each independently a fluorine atom or a hydrogen atom, y is independently an integer of 0 to 16 for each unit, a', b', and c' are each independently an integer of 0 or 1 or more, d' is an integer of 2 or more, and an order of repeating units in parentheses with subscript a', b', c', or d' is arbitrary in the formula.

12. The method according to claim 11, wherein the perfluoropolyoxyalkylene peroxide compound is a compound of formula (I)

wherein a and b are each independently an integer of 0 or more and 100 or less, and c and d are each independently an integer of 1 or more and 1000 or less, and the perfluoropolyoxyalkylene compound is a compound of formula (II)

wherein a' and b' are each independently an integer of 0 or more and 100 or less, and c' and d' are each independently an integer of 1 or more and 1000 or less.

13. The method according to claim 2, wherein the oxygen source is O$_2$, CO, a carbonate salt, a carboxylic acid, or a carboxylate ester.

14. The method according to claim 2, wherein the oxygen source is a carboxylic acid or a carboxylate ester.

15. The method according to claim 11, wherein a perfluoropolyoxyalkylene compound of formula (II) wherein $R^3$ is $-C_yF_{2y}-COOCH_3$ or $-C_yF_{2y}-COOH$, and/or $R^4$ is $-C_yF_{2y}-COOCH_3$ or $-C_yF_{2y}-COOH$ is used as the oxygen source.

* * * * *